United States Patent
Mishra et al.

(10) Patent No.: US 9,119,711 B2
(45) Date of Patent: Sep. 1, 2015

(54) METHODS AND SYSTEMS FOR MULTI-MONOPOLAR CURRENT STEERING IN AN AUDITORY PROSTHESIS SYSTEM

(75) Inventors: Lakshmi N. Mishra, Valencia, CA (US); Leonid M. Litvak, Los Angeles, CA (US); Manohar Joshi, Pune (IN)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 13/882,616

(22) PCT Filed: Oct. 28, 2011

(86) PCT No.: PCT/US2011/058289
§ 371 (c)(1),
(2), (4) Date: Apr. 30, 2013

(87) PCT Pub. No.: WO2012/058539
PCT Pub. Date: May 3, 2012

(65) Prior Publication Data
US 2013/0226297 A1   Aug. 29, 2013

Related U.S. Application Data

(60) Provisional application No. 61/408,585, filed on Oct. 30, 2010.

(51) Int. Cl.
*A61F 2/18* (2006.01)
*A61N 1/18* (2006.01)
*A61N 1/36* (2006.01)

(52) U.S. Cl.
CPC .............. *A61F 2/18* (2013.01); *A61N 1/36032* (2013.01)

(58) Field of Classification Search
CPC ..................................... A61F 2/18; A61N 1/18
USPC ..................... 623/10, 11, 11.11; 600/25, 559; 607/55–57, 137; 381/58–60, 328–331
See application file for complete search history.

(56) References Cited

U.S. PATENT DOCUMENTS 7,426,414 B1   9/2008   Litvak et al.

FOREIGN PATENT DOCUMENTS

| EP | 0247649 | 12/1987 |
|---|---|---|
| WO | WO-01/19304 | 3/2001 |
| WO | WO-2009/143553 | 12/2009 |

OTHER PUBLICATIONS

International Search Report and Written Opinion received in International Application No. PCT/US2011/058289, dated Jan. 5, 2012.

*Primary Examiner* — Yashita Sharma
(74) *Attorney, Agent, or Firm* — ALG Intellectual Property, LLC

(57) ABSTRACT

An exemplary method includes a sound processor 1) mapping an analysis channel associated with a frequency band to a stimulation channel that comprises at least three electrodes communicatively coupled to an auditory prosthesis associated with a patient, 2) identifying a spectral peak included in an audio signal presented to the patient, the spectral peak having a peak frequency included in the frequency band, and 3) directing the auditory prosthesis to apply electrical stimulation representative of the spectral peak to a stimulation site associated with the peak frequency by simultaneously stimulating at least two of the at least three electrodes at substantially fifty percent or less of their respective most comfortable current levels (M levels) in accordance with a multi-monopolar current steering strategy. Corresponding methods and systems are also disclosed.

20 Claims, 11 Drawing Sheets

METHODS AND SYSTEMS FOR MULTI-MONOPOLAR CURRENT STEERING IN AN AUDITORY PROSTHESIS SYSTEM

RELATED APPLICATIONS

The present application claims priority to U.S. patent application No. 61/408,585 by Lakshmi N. Mishra et al., filed on Oct. 30, 2010, and entitled "Methods and Systems for Multi-Monopolar Current Steering in an Auditory Prosthesis System" the contents of which are hereby incorporated by reference in their entirety.

BACKGROUND INFORMATION

Compliance voltage in an auditory prosthesis (e.g., an implantable cochlear stimulator) governs a maximum level of stimulation current that can be delivered by the auditory prosthesis via one or more electrodes to one or more stimulation sites within a patient (e.g., within the cochlea of the patient). A compliance voltage that is higher than absolutely necessary to generate and deliver a desired stimulation current causes the auditory prosthesis to operate in an inefficient manner. For example, the excess compliance voltage contributes to power loss that results in a reduced battery life of the auditory prosthesis. On the other hand, a compliance voltage less than that which is needed to generate and deliver a desired stimulation current inhibits optimal stimulation performance by the auditory prosthesis. For example, a sub-optimal compliance voltage limits the maximum stimulation rate at which the auditory prosthesis may apply stimulation current to the one or more stimulation sites, causes undesirable stimulation artifacts, and diminishes an overall experience of the patient with the auditory prosthesis. Hence, it is desirable to maintain a compliance voltage at which an auditory prosthesis operates at a level that optimizes battery life without sacrificing auditory prosthesis performance.

SUMMARY

An exemplary method includes a sound processor 1) mapping an analysis channel associated with a frequency band to a stimulation channel that comprises at least three electrodes communicatively coupled to an auditory prosthesis associated with a patient, 2) identifying a spectral peak included in an audio signal presented to the patient, the spectral peak having a peak frequency included in the frequency band, and 3) directing the auditory prosthesis to apply electrical stimulation representative of the spectral peak to a stimulation site associated with the peak frequency by simultaneously stimulating at least two of the at least three electrodes at substantially fifty percent or less of their respective most comfortable current levels ("M levels") in accordance with a multi-monopolar current steering strategy.

An exemplary system includes a mapping facility configured to map an analysis channel associated with a frequency band to a stimulation channel that comprises at least three electrodes communicatively coupled to an auditory prosthesis associated with a patient, a spectral analysis facility communicatively coupled to the mapping facility and configured to identify a spectral peak included in an audio signal presented to the patient, the spectral peak having a peak frequency included in the frequency band, and a stimulation strategy facility communicatively coupled to the spectral analysis facility and configured to direct the auditory prosthesis to apply electrical stimulation representative of the spectral peak to a stimulation site associated with the peak frequency by simultaneously stimulating at least two of the at least three electrodes at substantially fifty percent or less of their respective M levels in accordance with a multi-monopolar current steering strategy.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
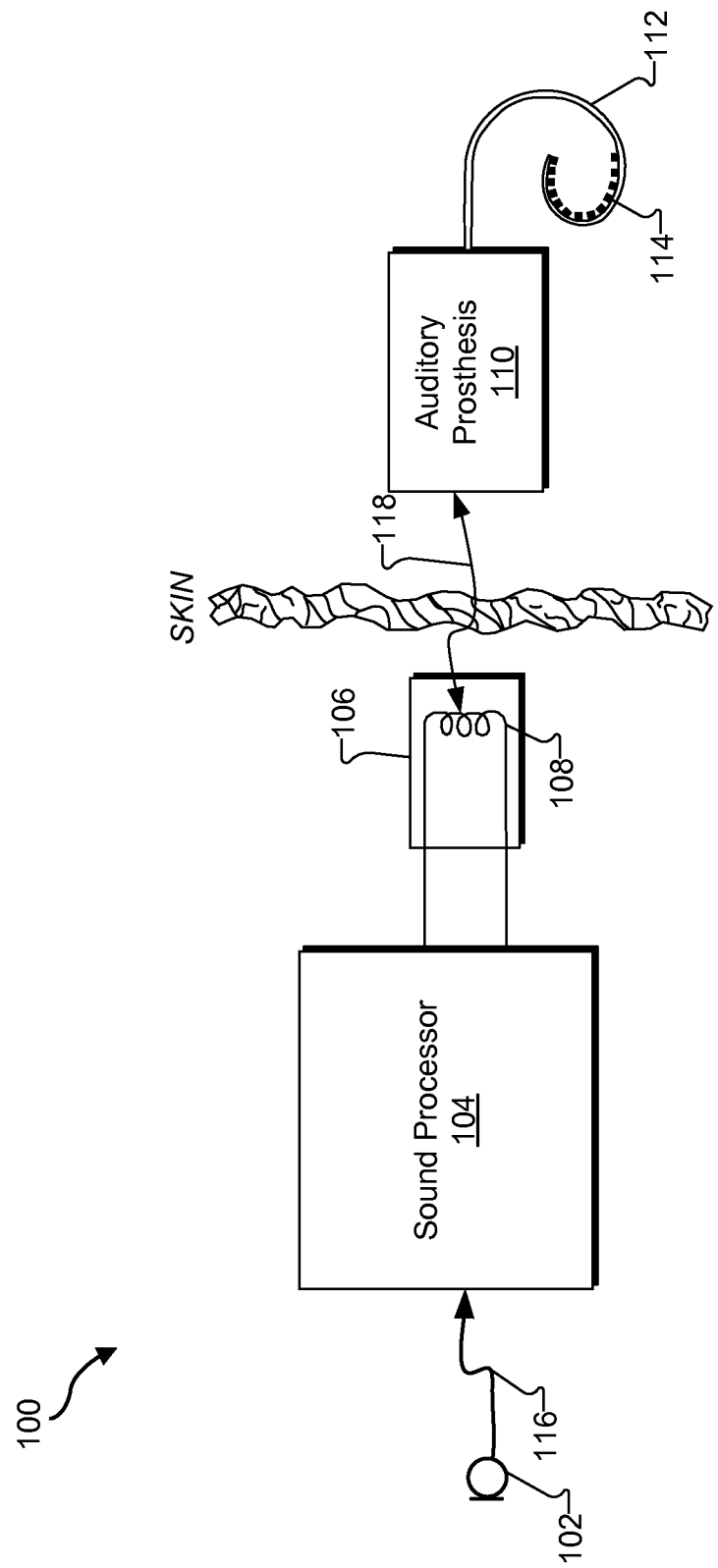
FIG. 1 illustrates an exemplary auditory prosthesis system according to principles described herein.

Methods and systems for multi-monopolar current steering in an auditory prosthesis system are described herein. In some examples, a sound processor may map an analysis channel associated with a frequency band to a stimulation channel that comprises at least three electrodes communicatively coupled to an auditory prosthesis associated with a patient. The sound processor may be further configured to identify a spectral peak included in an audio signal presented to the patient. As will be described below, the spectral peak has a peak frequency included in the frequency band. The sound processor may then direct the auditory prosthesis to apply electrical stimulation representative of the spectral peak to a stimulation site associated with the peak frequency by simultaneously stimulating at least two of the at least three electrodes at substantially fifty percent or less of their respective most comfortable current levels ("M levels") in accordance with a multi-monopolar current steering strategy.

As used herein, an "M level" associated with an electrode represents a most comfortable level of stimulation current which, when applied to the electrode, produces a sensed perception of sound by an auditory prosthesis patient that is comfortably loud, but not so loud that the perceived sound is uncomfortable. M levels may vary from electrode to electrode, although adjacent electrodes often have substantially similar M levels. M levels also vary from patient to patient. Therefore, M levels associated with electrodes implanted in a patient may be determined when fitting the auditory prosthesis to the patient and/or at any other time as may serve a particular implementation.

As used herein, a "multi-monopolar current steering strategy" refers to a current steering strategy in which an analysis channel is mapped to a stimulation channel having three or more electrodes. In accordance with the multi-monopolar current steering strategy, electrical stimulation is applied to a stimulation site by simultaneously stimulating at least two of the electrodes in the stimulation channel with stimulation current that is substantially equal in phase. In this manner, as will be described in more detail below, effective stimulation of the stimulation site may be achieved by stimulating the at least two electrodes at substantially fifty percent or less of their respective M levels.

To illustrate, in a "tri-monopolar current steering strategy," an analysis channel may be mapped to a stimulation channel that includes a first electrode, a second electrode, and a third electrode. The first electrode may correspond to a low cutoff frequency in the analysis channel, the second electrode may correspond a center frequency in the analysis channel, and the third electrode may correspond to a high cutoff frequency in the analysis channel. In accordance with the tri-monopolar current steering strategy, at least two of the three electrodes are simultaneously stimulated at substantially fifty percent or less of their respective M levels in order to represent spectral content included in the analysis channel.

As will be described in more detail below, the methods and systems described herein enable the auditory prosthesis to operate at a compliance voltage substantially equal to fifty percent or less of a compliance voltage required for a maximum M level associated with the three electrodes (i.e., the highest M level out of the M levels associated with each respective electrode). In this manner, battery life of the auditory prosthesis may be extended without sacrificing stimulation rate.

FIG. 1 illustrates an exemplary auditory prosthesis system 100. Auditory prosthesis system 100 may include a microphone 102, a sound processor 104, a headpiece 106 having a coil 108 disposed therein, an auditory prosthesis 110, and a lead 112 with a plurality of electrodes 114 disposed thereon. Additional or alternative components may be included within auditory prosthesis system 100 as may serve a particular implementation.

As shown in FIG. 1, microphone 102, sound processor 104, and headpiece 106 may be located external to an auditory prosthesis patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct auditory prosthesis 110 to generate and apply electrical stimulation (also referred to herein as "stimulation current") to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the audio signal detected by microphone 102 in accordance with a selected sound processing strategy to generate appropriate stimulation parameters for controlling auditory prosthesis 110. Sound processor 104 may include or be implemented by a behind-the-ear ("BTE") unit, a portable speech processor ("PSP"), and/or any other sound processing unit as may serve a particular implementation. Exemplary components of sound processor 104 will be described in more detail below.

Sound processor 104 may be configured to transcutaneously transmit one or more control parameters and/or one or more power signals to auditory prosthesis 110 with coil 108 by way of a communication link 118. These control parameters may be configured to specify one or more stimulation parameters, operating parameters, and/or any other parameter by which auditory prosthesis 110 is to operate as may serve a particular implementation. Exemplary control parameters include, but are not limited to, stimulation current levels, volume control parameters, program selection parameters, operational state parameters (e.g., parameters that turn a sound processor and/or an auditory prosthesis on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters. Additional features of sound processor 104 will be described in more detail below.

As shown in FIG. 1, coil 108 may be housed within headpiece 106, which may be affixed to a patient's head and positioned such that coil 108 is communicatively coupled to a corresponding coil included within auditory prosthesis 110. In this manner, control parameters and power signals may be wirelessly transmitted between sound processor 104 and auditory prosthesis 110 via communication link 118. It will be understood that data communication link 118 may include a bi-directional communication link and/or one or more dedicated uni-directional communication links. In some alternative embodiments, sound processor 104 and auditory prosthesis 110 may be directly connected with one or more wires or the like.

Auditory prosthesis 110 may include any type of implantable stimulator that may be used in association with the systems and methods described herein. For example, auditory prosthesis 110 may include an implantable cochlear stimulator. In some alternative implementations, auditory prosthesis 110 may include a brainstem implant and/or any other type of auditory prosthesis that may be implanted within a patient and configured to apply stimulation to one or more stimulation sites located along an auditory pathway of a patient.

In some examples, auditory prosthesis 110 may be configured to generate electrical stimulation representative of an audio signal detected by microphone 102 in accordance with one or more stimulation parameters transmitted thereto by sound processor 104. Auditory prosthesis 110 may be further configured to apply the electrical stimulation to one or more stimulation sites within the patient via one or more electrodes 114 disposed along lead 112. In some examples, auditory prosthesis 110 may include a plurality of independent current sources each associated with a channel defined by one or more of electrodes 114. In this manner, different stimulation current levels may be applied to multiple stimulation sites simultaneously by way of multiple electrodes 114. In such examples, auditory prosthesis system 100 may be referred to as a "multi-channel auditory prosthesis system."

Figure 2:
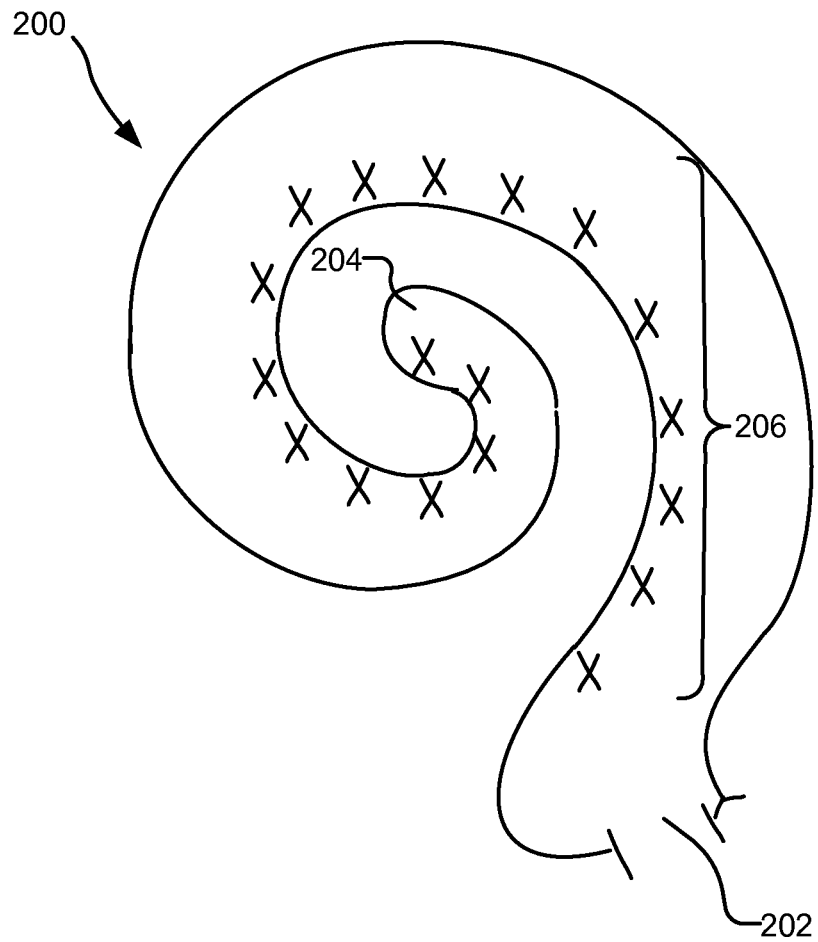
FIG. 2 illustrates a schematic structure of the human cochlea.

To facilitate application of the electrical stimulation generated by auditory prosthesis 110, lead 112 may be inserted within a duct of the cochlea such that electrodes 114 are in communication with one or more stimulation sites within the cochlea. FIG. 2 illustrates a schematic structure of the human cochlea 200 into which lead 112 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Auditory prosthesis system 100 may therefore be configured to apply electrical stimulation to different locations within the cochlea 200 (e.g., different locations along the auditory nerve tissue 206) to provide a sensation of hearing.

Alternatively, lead 112 may be implanted within a patient such that electrodes 114 are in communication with one or more stimulation sites otherwise located along the auditory pathway. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 3:
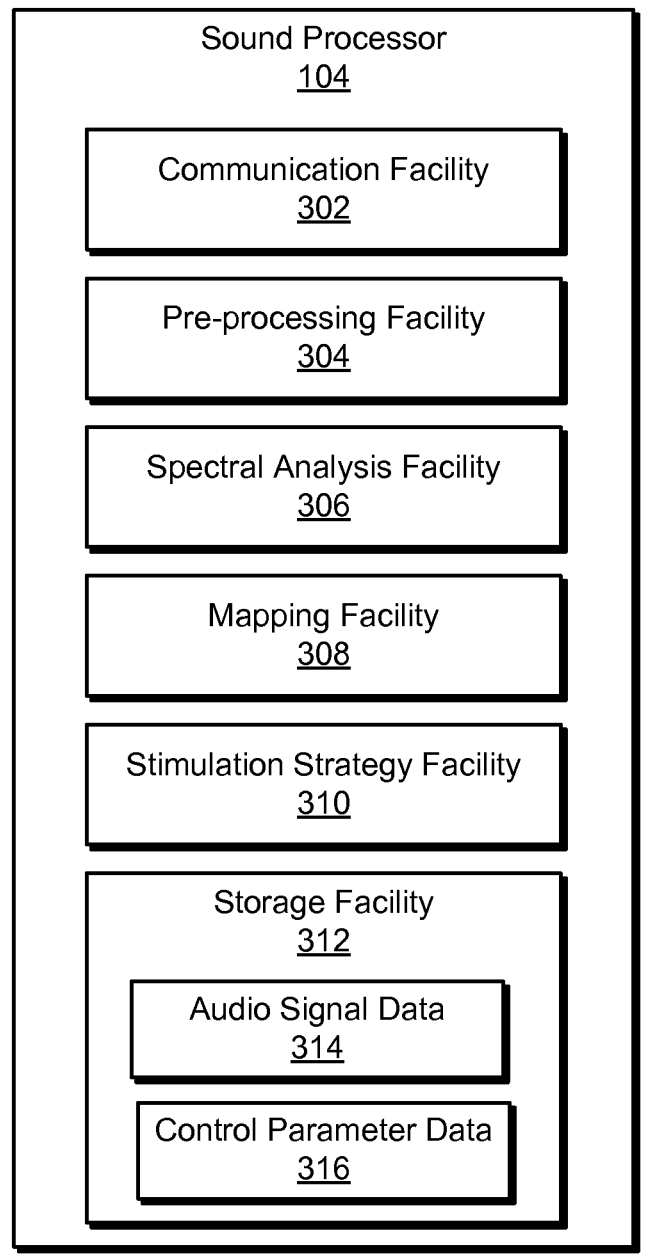
FIG. 3 illustrates exemplary components of a sound processor according to principles described herein.

FIG. 3 illustrates exemplary components of sound processor 104. As shown in FIG. 3, sound processor 104 may include a communication facility 302, a pre-processing facility 304, a spectral analysis facility 306, a mapping facility 308, a stimulation strategy facility 310, and a storage facility 312, which may be in communication with one another using any suitable communication technologies. Each of these facilities 302-312 may include any combination of hardware, software, and/or firmware as may serve a particular implementation. For example, one or more of facilities 302-312 may include a computing device or processor configured to perform one or more of the functions described herein. Facilities 302-312 will now be described in more detail.

Communication facility 302 may be configured to facilitate communication between sound processor 104 and auditory prosthesis 110. For example, communication facility 302 may include transceiver components configured to wirelessly transmit data (e.g., control parameters and/or power signals) to auditory prosthesis 110 and/or wirelessly receive data from auditory prosthesis 110.

Pre-processing facility 304 may be configured to receive one or more audio signals and perform various signal processing operations on the one or more audio signals. For example, pre-processing facility 304 may amplify a detected audio signal, convert the audio signal to a digital signal, filter the digital signal with a pre-emphasis filter, subject the digital signal to automatic gain control, and/or perform one or more other signal processing operations on the detected audio signal.

Spectral analysis facility 306 may be configured to divide an audio signal into a plurality of analysis channels each containing a frequency domain signal representative of a distinct frequency portion of the audio signal. For example, spectral analysis facility 306 may include a plurality of bandpass filters configured to divide the audio signal into a plurality of frequency channels or bands. Additionally or alternatively, spectral analysis facility 306 may be configured to convert the audio signal from a time domain into a frequency domain and then divide the resulting frequency bins into the plurality of analysis channels. To this end, spectral analysis facility 306 may include one or more components configured to apply a Discrete Fourier Transform (e.g., a Fast Fourier Transform ("FFT")) to the audio signal.

Spectral analysis facility 306 may be configured to divide the audio signal into any number of analysis channels as may serve a particular implementation. In some examples, the total number of analysis channels is set to be less than or equal to a total number of stimulation channels through which electrical stimulation representative of the audio signal is applied to an auditory prosthesis patient.

Spectral analysis facility 306 may be further configured to analyze an acoustic spectrum of the audio signal and identify one or more spectral peaks included therein. For example, spectral analysis facility 306 may be configured to identify a spectral peak included in one or more analysis channels.

Spectral analysis facility 306 may be configured to identify spectral peaks in any suitable manner. In some examples, spectral analysis facility 306 may identify a spectral peak by detecting a maximum energy level included in a particular analysis channel and identifying a frequency associated with the maximum energy level. Other spectral analysis heuristics may be used by spectral analysis facility 306 to identify spectral peaks as may serve a particular implementation.

Mapping facility 308 may be configured to map each analysis channel to a particular stimulation channel used by auditory prosthesis 110 to apply electrical stimulation to one or more stimulation sites. In some examples, as will be described in more detail below, each stimulation channel may include at least three electrodes 114. In this manner, a tri-monopolar or multi-polar current steering strategy may be used to deliver the electrical stimulation.

Mapping facility 308 may be further configured to map the signals within the analysis channels to electrical stimulation pulses to be applied to a patient via one or more stimulation channels. For example, signal levels of the signals within the analysis channels may be mapped to amplitude values used to define electrical stimulation pulses that are applied to the patient by auditory prosthesis 110 via one or more corresponding stimulation channels. Mapping facility 308 may be further configured to perform additional processing of the signals contained within the analysis channels, such as signal compression.

Stimulation strategy facility 310 may be configured to select a particular stimulation configuration in which auditory prosthesis 110 operates to generate and apply electrical stimulation representative of various spectral components of an audio signal. To this end, stimulation strategy facility 310 may generate one or more stimulation parameters based on the frequency domain signals within the analysis channels. For example, stimulation strategy facility 310 may generate one or more stimulation parameters configured to direct cochlear prosthesis 110 to apply electrical stimulation representative of an identified spectral peak to a stimulation site by simultaneously stimulating two or more electrodes at substantially fifty percent or less of their respective most comfortable current levels ("M levels") in accordance with a tri-monopolar current steering strategy.

Storage facility 312 may be configured to maintain audio signal data 314 representative of an audio signal received by pre-processing facility 304 and control parameter data 316 representative of one or more control parameters, which may include one or more stimulation parameters to be transmitted from sound processor 104 to auditory prosthesis 110. Storage facility 312 may be configured to maintain additional or alternative data as may serve a particular implementation.

Figure 4:
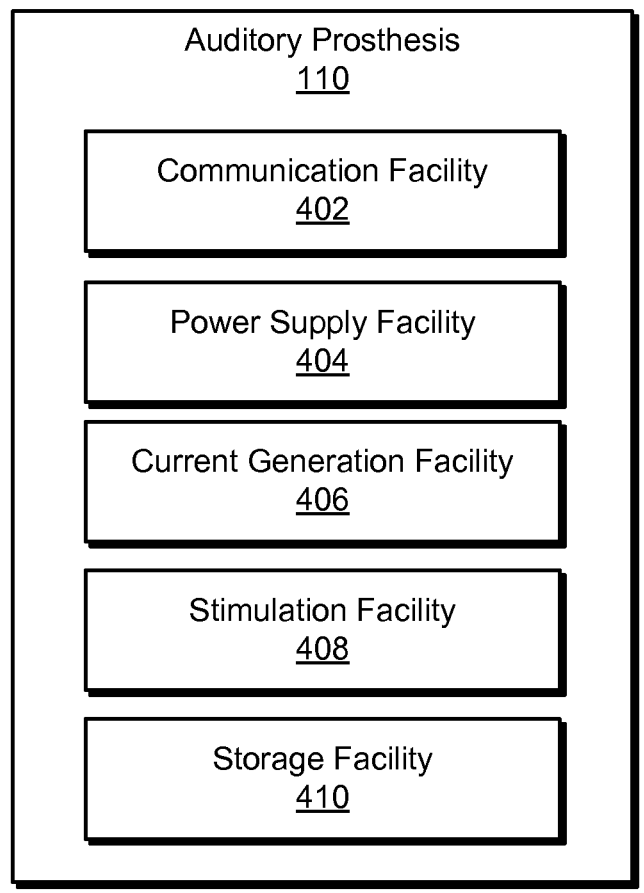
FIG. 4 illustrates exemplary components of an auditory prosthesis according to principles described herein.

FIG. 4 illustrates exemplary components of auditory prosthesis 110. As shown in FIG. 4, auditory prosthesis 110 may include a communication facility 402, a power supply facility 404, a current generation facility 406, a stimulation facility 408, and a storage facility 410, which may be in communication with one another using any suitable communication technologies. Each of these facilities 402-410 may include any combination of hardware, software, and/or firmware as may serve a particular application. For example, one or more of facilities 402-410 may include a computing device or processor configured to perform one or more of the functions described herein. Facilities 402-410 will now be described in more detail.

Communication facility 402 may be configured to facilitate communication between auditory prosthesis 110 and sound processor 104. For example, communication facility 402 may include one or more coils configured to receive control signals and/or power signals from sound processor 104. Communication facility 402 may additionally or alternatively be configured to transmit one or more status signals and/or other data to sound processor 104.

Power supply facility 404 may be configured to provide power to various components included within auditory prosthesis 110. To this end, power supply facility 404 may be configured to derive a compliance voltage from a power signal received from sound processor 104. The compliance voltage may be used by current generation facility 404 to generate stimulation current and/or by any other component within auditory prosthesis 110.

Current generation facility 406 may be configured to generate stimulation current in accordance with one or more stimulation parameters received from sound processor 104. To this end, current generation facility 406 may include one or more current generators and/or any other circuitry configured to facilitate generation of stimulation current. For example, current generation facility 406 may include an array of independent current generators each corresponding to a distinct electrode or channel. As discussed previously, a maximum stimulation current level that each current generator is capable of producing is dependent in part on the compliance voltage produced by power supply facility 404.

Stimulation facility 408 may be configured to facilitate application of the stimulation current generated by current generation facility 406 to one or more stimulation sites within the patient in accordance with one or more stimulation parameters received from sound processor 104. For example, stimulation facility 406 may be configured to apply electrical stimulation representative of one or more spectral peaks of an audio signal as identified by spectral analysis facility 306 to at least one stimulation site within the auditory prosthesis patient in accordance with a tri-monopolar or a multi-monopolar current steering strategy. To this end, stimulation facility 408 may be configured to interface with one or more electrodes disposed on a lead that may be inserted within the patient (e.g., within the cochlea).

Storage facility 410 may be configured to maintain data generated and/or utilized by auditory prosthesis 110. For example, storage facility 410 may maintain data representative of one or more stimulation parameters configured to define the stimulation current generated and applied by auditory prosthesis 110.

Figure 5:
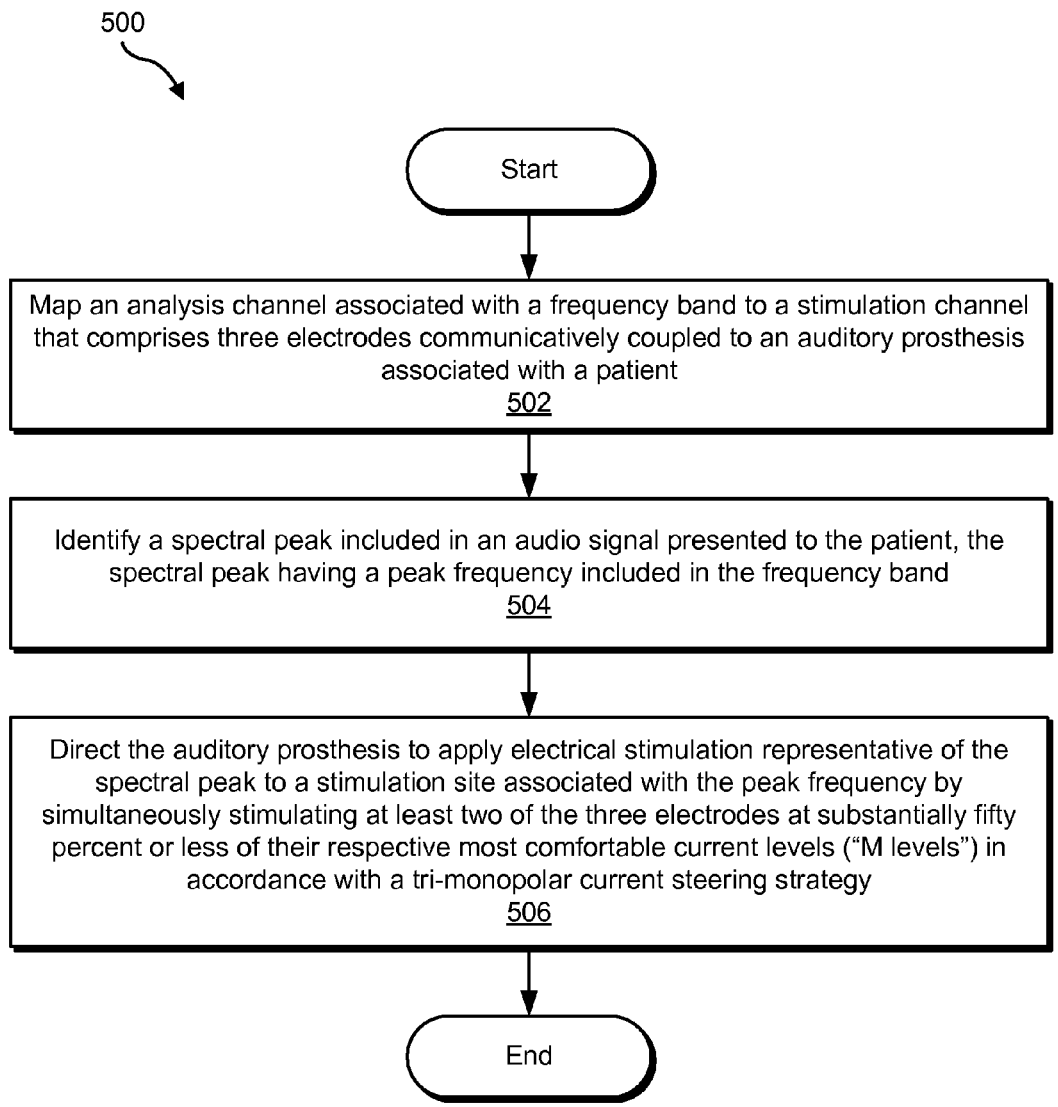
FIG. 5 illustrates an exemplary tri-monopolar current steering method according to principles described herein.

FIG. 5 illustrates an exemplary tri-monopolar current steering method 500. While FIG. 5 illustrates exemplary steps according to one embodiment, other embodiments may omit, add to, reorder, and/or modify any of the steps shown in FIG. 5. One or more of the steps shown in FIG. 5 may be performed by any component or combination of components of sound processor 104.

In step 502, an analysis channel associated with a frequency band is mapped to a stimulation channel that comprises three electrodes communicatively coupled to an auditory prosthesis associated with a patient. The analysis channel may be mapped to the stimulation channel in any suitable manner as may serve a particular implementation.

Figure 6:
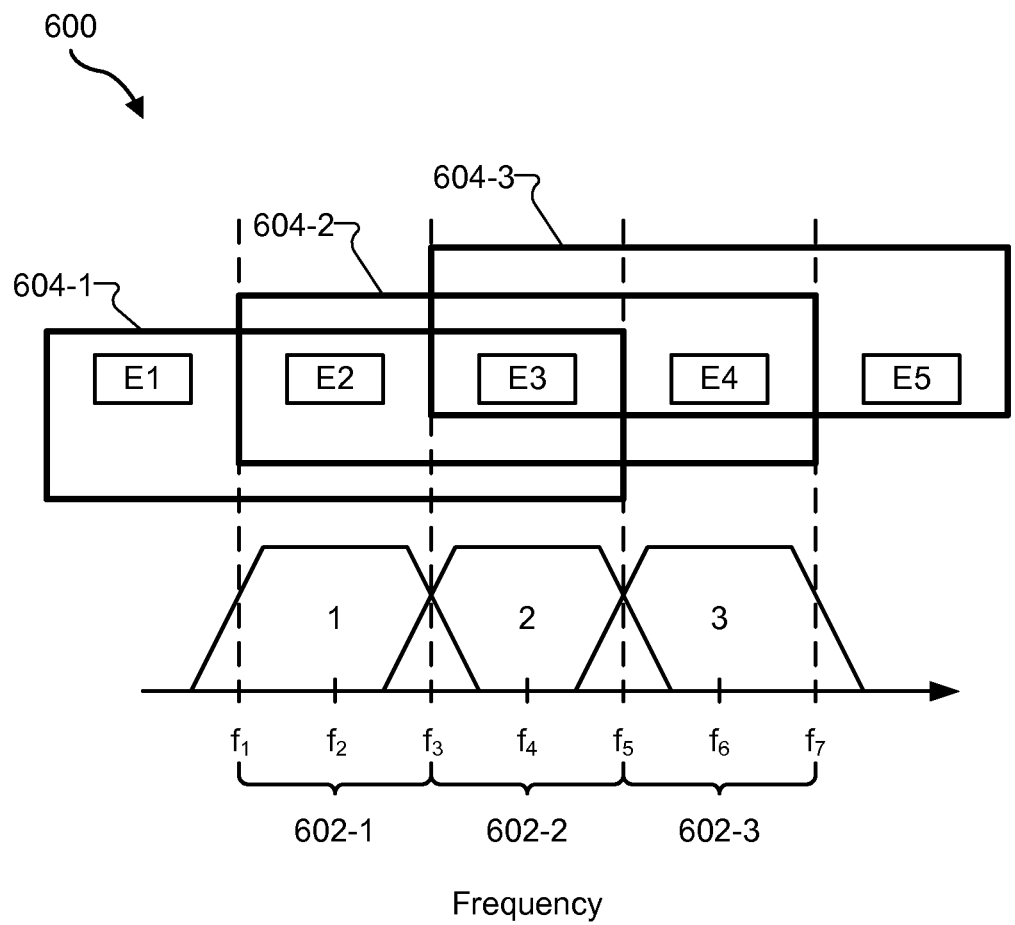
FIG. 6 shows an exemplary mapping of analysis channels to stimulation channels according to principles described herein.

To illustrate, FIG. 6 shows an exemplary mapping 600 of analysis channels 602 (e.g., analysis channels 602-1 through 602-3) to stimulation channels 604 (e.g., stimulation channels 604-1 through 604-3) for a five electrode configuration. FIG. 6 shows five electrodes E1 through E5 for illustrative purposes only. It will be recognized that mapping 600 may be associated with any other number of electrodes as may serve a particular implementation.

As shown in FIG. 6, each analysis channel 602 may be associated with a particular frequency band defined by a low cutoff frequency and a high cutoff frequency. For example, analysis channel 602-1 is defined by a low cutoff frequency of $f_1$ and a high cutoff frequency of $f_3$, analysis channel 602-2 is defined by a low cutoff frequency of $f_3$ and a high cutoff frequency of $f_5$, and analysis channel 602-3 is defined by a low cutoff frequency of $f_5$ and a high cutoff frequency of $f_7$. Each analysis channel 602 may have a center frequency associated therewith. For example, analysis channel 602-1 has a center frequency of $f_2$, analysis channel 602-2 has a center frequency of $f_4$, and analysis channel 602-3 has a center frequency of $f_6$.

As illustrated in FIG. 6, each stimulation channel 604 comprises three electrodes. For example, stimulation channel 604-1 comprises electrodes E1-E3, stimulation channel 604-2 comprises electrodes E2-E4, and stimulation channel 604-3 comprises electrodes E3-E5. Hence, in an n-electrode system, there may be n-2 stimulation channels 604.

Each electrode may be positioned at a location within the patient (e.g., within the cochlea) that corresponds to a particular frequency. For example, electrode E2 is positioned at a location that corresponds to center frequency $f_2$ and may therefore be referred to as a "center electrode." Stimulation of electrode E2 by itself may result in an excitation field having a centroid (i.e., peak) located at frequency $f_2$. However, electrodes E1 and E3, referred to herein as "flanking electrodes" because they flank center electrode E2, are positioned at locations within the cochlea that correspond to frequencies outside the frequency band associated with analysis channel 602-1. For example, as illustrated in FIG. 6, electrode $E_1$ is positioned at a location associated with a frequency that is lower than low cutoff frequency $f_1$ and electrode E3 is positioned at a location associated with a frequency that is higher than high cutoff frequency $f_3$. As will be described in more detail below, even though flanking electrodes E1 and E3 are located outside the frequency band associated with analysis channel 602-1, simultaneous stimulation of one or both of flanking electrodes E1 and E3 along with center electrode E2 may result in an excitation field having a centroid located within the frequency band associated with analysis channel 602-1.

In some examples, the electrodes included in each stimulation channel 604 may be located sequentially (i.e., adjacent one to another) along an electrode lead implanted in an auditory prosthesis patient. As mentioned above, adjacent electrodes may have substantially equivalent M levels. Alternatively, as will be described in more detail below, the electrodes included in one or more of stimulation channel 604 are non-adjacent one to another (e.g., in the case of a disabled electrode).

In the example of FIG. 6, analysis channel 602-1 is mapped to stimulation channel 604-1, analysis channel 602-2 is mapped to stimulation channel 604-2, and analysis channel 602-3 is mapped to stimulation channel 604-3. In other words, sound processor 104 may direct auditory prosthesis 110 to apply electrical stimulation representative of spectral content included in analysis channel 602-1 by way of stimulation channel 604-1, spectral content included in analysis channel 602-2 by way of stimulation channel 604-2, and spectral content included in analysis channel 602-3 by way of stimulation channel 604-3.

Returning to FIG. 5, in step 504, a spectral peak included in an audio signal presented to the patient is identified. The spectral peak may be identified in any of the ways described herein and may have a peak frequency included in a frequency band associated with the analysis channel mapped in step 502. For example, the peak frequency may be included in the frequency band associated with analysis channel 602-1.

In step 506, the auditory prosthesis is directed to apply electrical stimulation representative of the spectral peak identified in step 504 to a stimulation site associated with the peak frequency by simultaneously stimulating at least two of the three electrodes included in the analysis channel's corresponding stimulation channel at substantially fifty percent or less of their respective M levels in accordance with a tri-monopolar current steering strategy. Step 506 may be performed in any suitable manner as may serve a particular implementation.

To illustrate, sound processor 104 may direct auditory prosthesis 110 to apply electrical stimulation representative of a spectral peak having a peak frequency included in the frequency band associated with analysis channel 602-1 by simultaneously stimulating at least two of the three electrodes included in stimulation channel 604-1. The at least two electrodes may be stimulated at substantially fifty percent or less of their respective M levels in accordance with a tri-monopolar current steering strategy. In this manner, as described above, auditory prosthesis 110 may operate (i.e., sound processor 104 may direct auditory prosthesis 110 to operate) at a compliance voltage substantially equal to fifty percent of the compliance voltage required if one or more of the electrodes were stimulated at one-hundred percent of their respective M levels and thereby minimize power usage by auditory prosthesis 110.

For example, the spectral peak may have a peak frequency substantially equal to the center frequency (i.e., $f_2$) of the frequency band associated with analysis channel 602-1. Sound processor 104 may direct auditory prosthesis 110 to apply electrical stimulation representative of the spectral peak by directing auditory prosthesis 110 to stimulate the electrodes included in corresponding stimulation channel 604-1 in a manner illustrated in FIG. 7.

Figure 7:
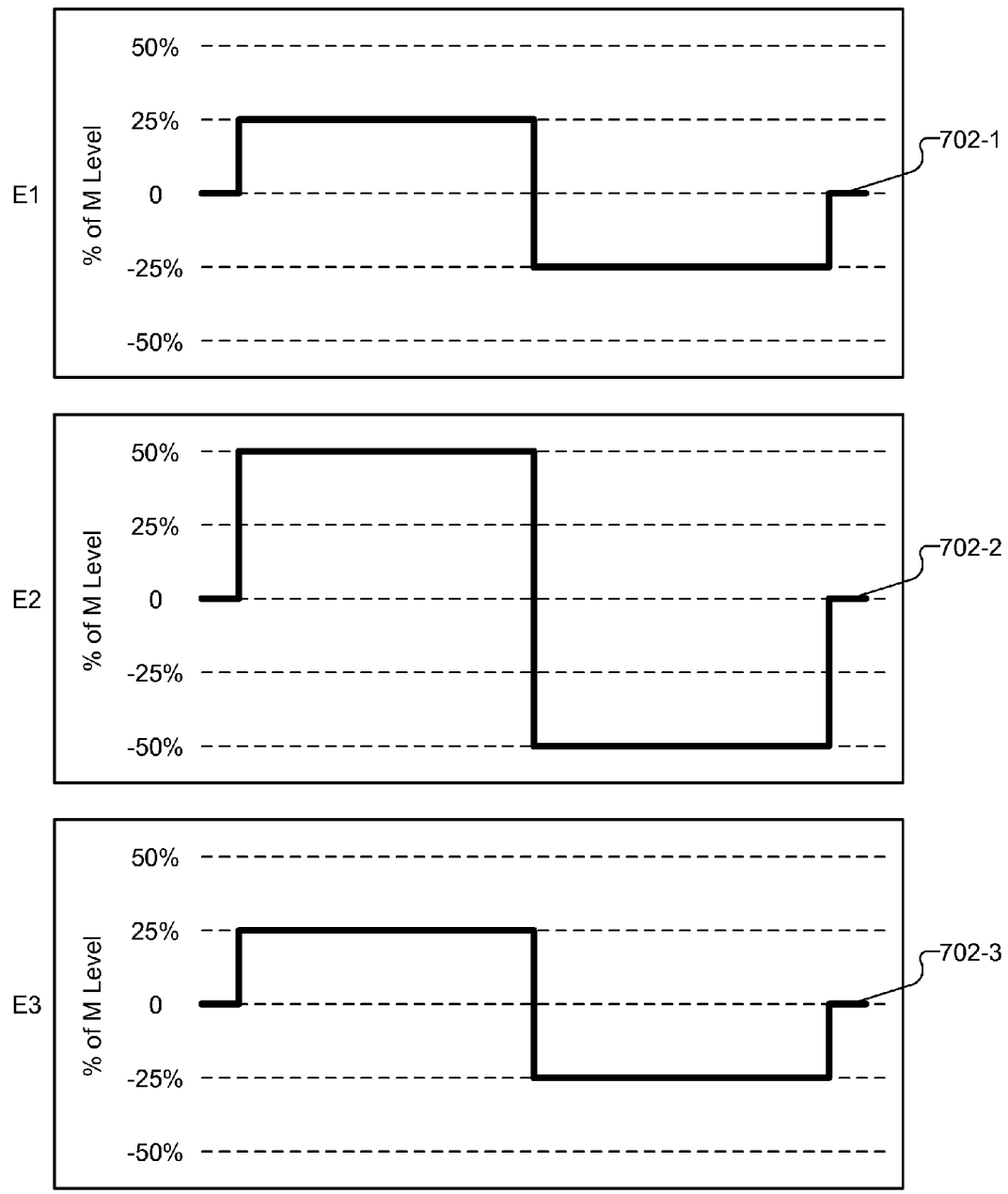
FIGS. 7-9 illustrate exemplary stimulation current waveforms according to principles described herein.

FIG. 7 illustrates exemplary stimulation current waveforms 702 (e.g., 702-1 through 702-3) that may be applied to electrodes E1, E2, and E3, respectively, in order to represent a spectral peak having a peak frequency substantially equal to center frequency $f_2$. As shown by waveform 702-2, sound processor 104 may direct auditory prosthesis 110 to stimulate electrode E2 at a current level substantially equal to fifty percent of the M level associated with electrode E2. Likewise, as shown by waveforms 702-1 and 702-3, sound processor 104 may simultaneously direct auditory prosthesis 110 to stimulate each of electrodes E1 and E3 at a current levels substantially equal to twenty-five percent of their respective M levels. Simultaneous stimulation of electrodes E1-E3, as illustrated in FIG. 7, may result in an excitation field having a centroid located at center frequency $f_2$.

Alternatively, the spectral peak may have a peak frequency substantially equal to the low cutoff frequency (i.e., $f_1$) of the frequency band associated with analysis channel 602-1. Sound processor 104 may direct auditory prosthesis 110 to apply electrical stimulation representative of the spectral peak by directing auditory prosthesis 110 to stimulate the electrodes included in corresponding stimulation channel 604-1 in a manner illustrated in FIG. 8.

Figure 8:
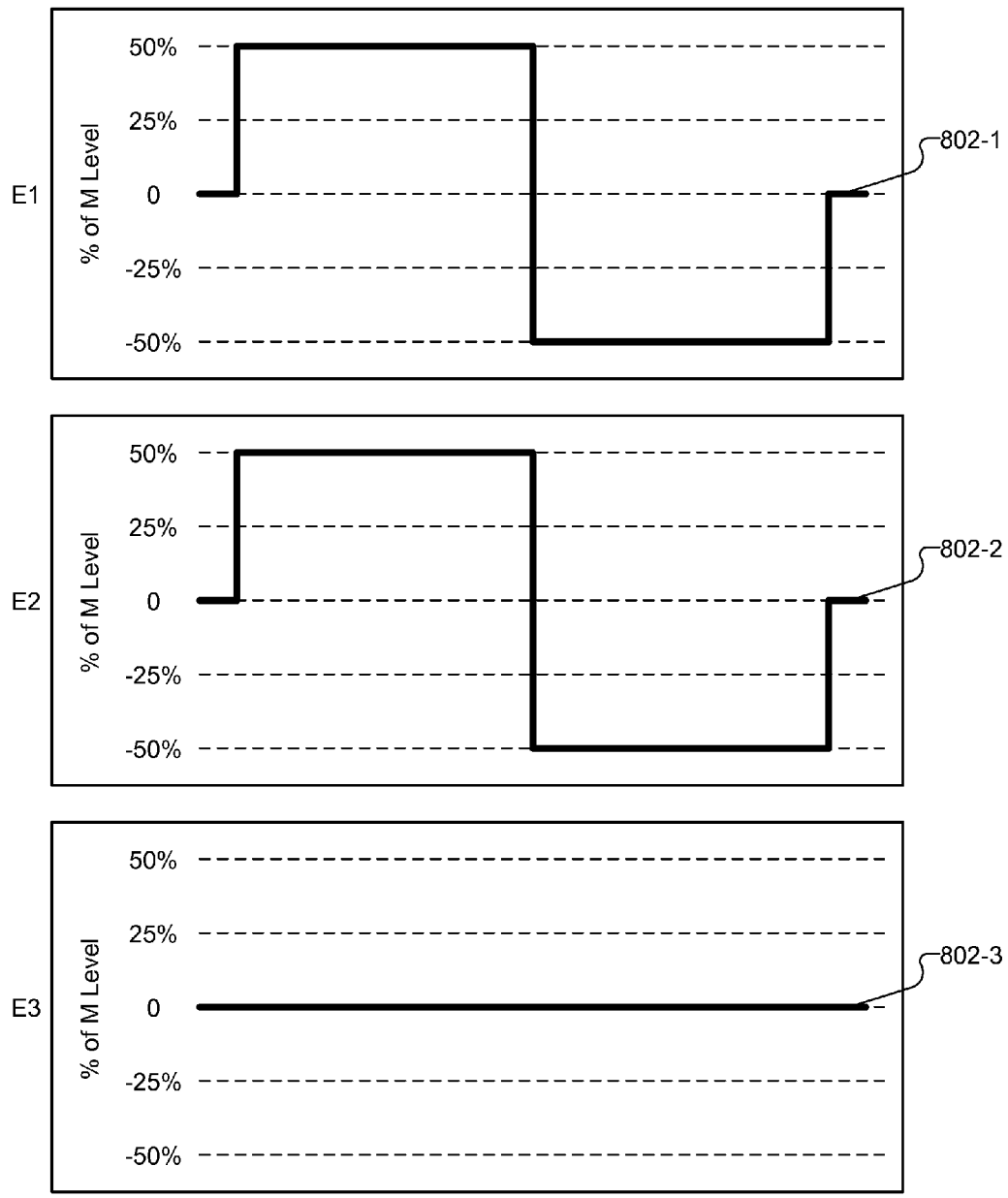

FIG. 8 illustrates exemplary stimulation current waveforms 802-1 and 802-2 that may be applied to electrodes E1 and E2, respectively, in order to represent a spectral peak having a peak frequency substantially equal to low cutoff frequency $f_1$. As shown by waveforms 802-1 and 802-2, sound processor 104 may direct auditory prosthesis 110 to simultaneously stimulate electrodes E1 and E2 at current levels substantially equal to fifty percent of their respective M levels. Sound processor may also direct auditory prosthesis 110 to not apply any stimulation current to electrode E3, as shown by flat line 802-3. Simultaneous stimulation of electrodes E1 and E2, as illustrated in FIG. 8, may result in an excitation field having a centroid located at low cutoff frequency $f_1$. In some examples, the centroid may be shifted right towards the center frequency $f_2$ by decreasing the current level applied to electrode E1 and increasing the current level applied to E3.

Alternatively, the spectral peak may have a peak frequency substantially equal to the high cutoff frequency (i.e., $f_3$) of the frequency band associated with analysis channel 602-1. Sound processor 104 may direct auditory prosthesis 110 to apply electrical stimulation representative of the spectral peak by directing auditory prosthesis 110 to stimulate the electrodes included in corresponding stimulation channel 604-1 in a manner illustrated in FIG. 9.

Figure 9:
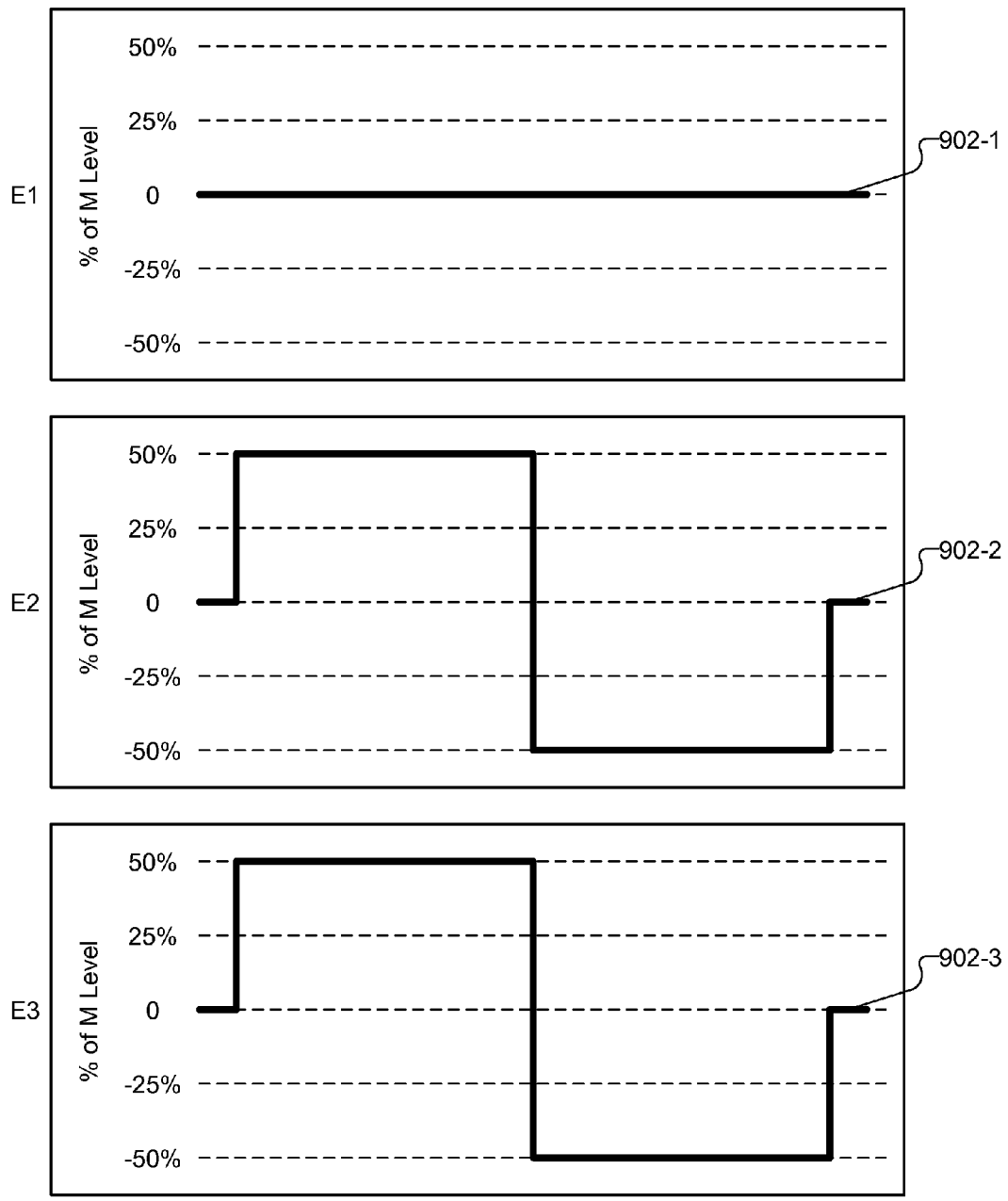

FIG. 9 illustrates exemplary stimulation current waveforms 902-2 and 902-3 that may be applied to electrodes E2 and E3, respectively, in order to represent a spectral peak having a peak frequency substantially equal to high cutoff frequency $f_3$. As shown by waveforms 902-2 and 902-3, sound processor 104 may direct auditory prosthesis 110 to simultaneously stimulate electrodes E2 and E3 at current levels substantially equal to fifty percent of their respective M levels. Sound processor may also direct auditory prosthesis 110 to not apply any stimulation current to electrode E1, as shown by flat line 902-1. Simultaneous stimulation of electrodes E2 and E3, as illustrated in FIG. 9, may result in an excitation field having a centroid located at high cutoff frequency $f_3$. In some examples, the centroid may be shifted left towards the center frequency $f_2$ by decreasing the current level applied to electrode E3 and increasing the current level applied to electrode E1.

As illustrated, the tri-monopolar current steering strategy described herein may be used to selectively generate an excitation field having a centroid located at any frequency within a frequency band associated with an analysis channel 602. However, it will be recognized that the lowest centroid that may be achieved using the tri-monopolar current steering strategy described herein is midway between the two lowest enabled electrodes. For example, with reference to FIG. 6, if electrode E1 is the lowest enabled electrode (e.g., the most apical electrode), the lowest centroid that may be achieved using the tri-monopolar current steering strategy described herein is midway between electrodes E1 and E2. Likewise, the highest centroid that may be achieved using the tri-monopolar current steering strategy described herein is midway between the two highest enabled electrodes. For example, with reference again to FIG. 6, if electrode E5 is the highest enabled electrode (e.g., the most basal electrode), the highest centroid that may be achieved using the tri-monopolar current steering strategy described herein is midway between electrodes E4 and E5.

Hence, in some examples, sound processor 104 may direct auditory prosthesis 110 to utilize phantom electrode stimulation to generate a centroid located lower than midway between electrodes E1 and E2 and higher than midway between electrodes E4 and E5. "Phantom electrode stimulation" refers to a stimulation strategy that may be used to expand a range of pitches or frequencies that may be presented to an auditory prosthesis patient. In phantom electrode stimulation, compensation current is applied to one or more compensating electrodes in order to produce sound having a pitch that is lower than a pitch associated with a particular electrode (e.g., the most apical electrode) or a sound having a pitch that is higher than a pitch associated with a particular electrode (e.g., the most basal electrode). Phantom electrode stimulation is more fully described in co-pending U.S. patent application Ser. No. 12/644,350, entitled "COMPENSATION CURRENT OPTIMIZATION FOR COCHLEAR IMPLANT SYSTEMS," filed Dec. 22, 2010, and incorporated herein by reference in its entirety.

In some instances, an electrode included in an array of electrodes may be or become disabled. As used herein, a "disabled" electrode refers to a malfunctioning electrode, an electrode that has been turned off, and/or an electrode that is not or cannot be stimulated for any other reason.

Figure 10:
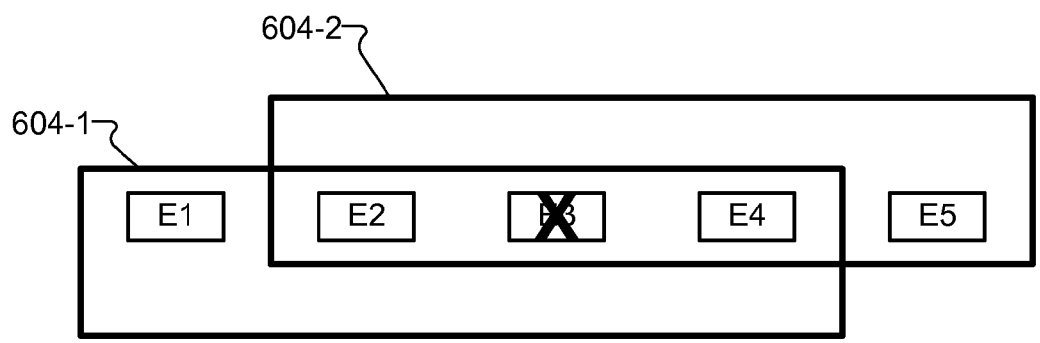
FIG. 10 illustrates an exemplary configuration wherein an electrode is disabled according to principles described herein.

In some examples, the multi-monopolar current steering strategies described herein may be configured to compensate for a disabled electrode. For example, FIG. 10 shows the same electrodes E1-E5 that are shown in FIG. 6. However, FIG. 10 shows that one of the electrodes, electrode E3, has become disabled (indicated by the "X" covering E3). Sound processor 104 may compensate for the disabled electrode by redefining the stimulation channels to not include the disabled electrode. For example, as shown in FIG. 10, sound processor 104 may redefine stimulation channel 604-1 to include electrodes E1, E2, and E4. Sound processor 104 may likewise redefine stimulation channel 604-2 to include electrodes E2, E4, and E5. The manner in which the enabled electrodes are stimulated may also be correspondingly adjusted to compensate for the disabled electrode.

In some examples, "limited current steering" may be employed in which a frequency band associated with a particular stimulation channel may be narrowed to result in a restricted current steering range. In this manner, the electrodes that make up the stimulation channel may be stimulated at stimulation levels even lower than fifty percent or less of their respective M levels.

It will be recognized that the systems and methods described herein are not limited to tri-monopolar current steering strategies. Rather, any multi-polar current steering strategy in which three or more electrodes are included in each stimulation channel may be used in accordance with the methods and systems described herein.

Figure 11:
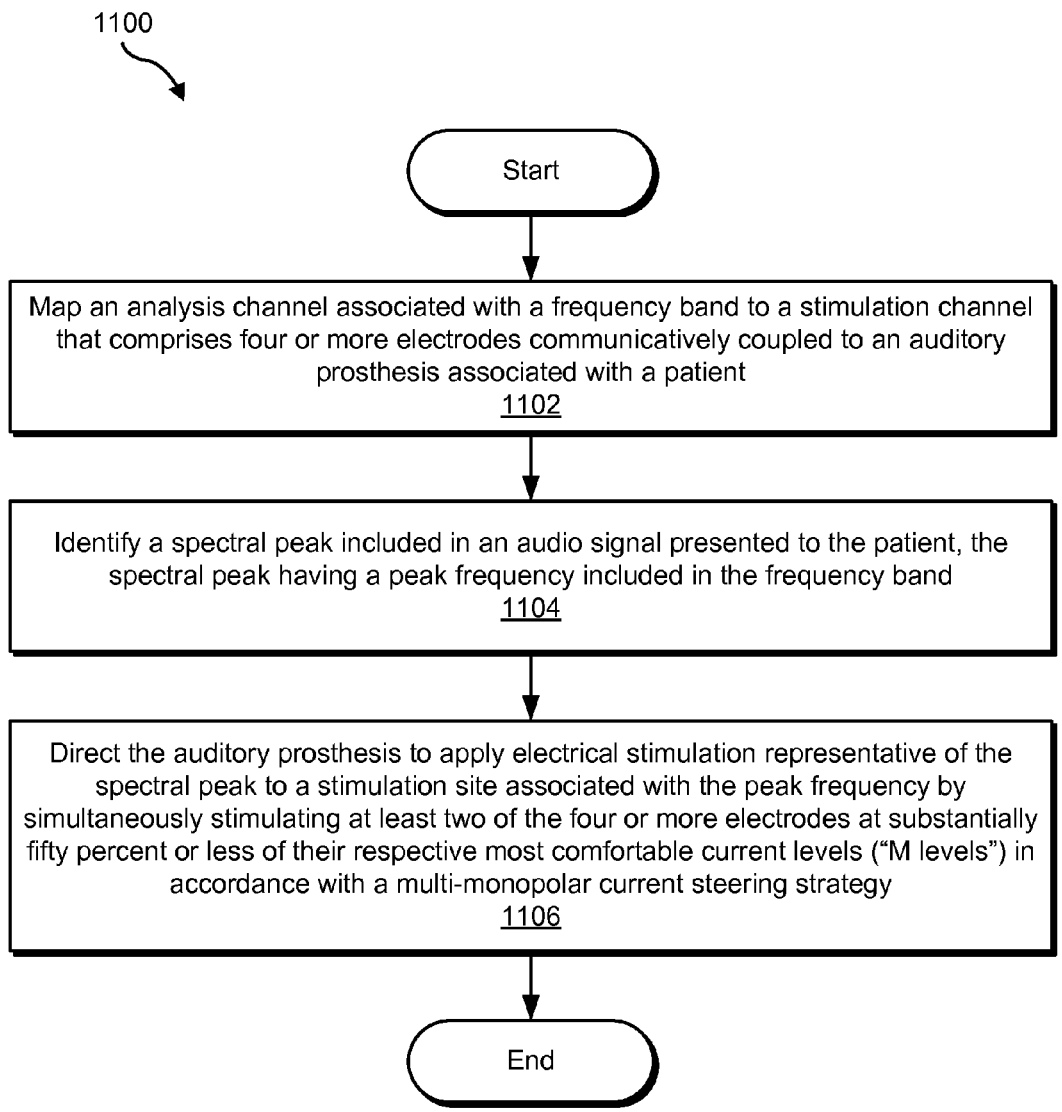
FIG. 11 illustrates an exemplary multi-monopolar current steering method according to principles described herein.

For example, FIG. 11 illustrates an exemplary multi-monopolar current steering method 1100 in which each stimulation channel includes four or more electrodes. While FIG. 11 illustrates exemplary steps according to one embodiment, other embodiments may omit, add to, reorder, and/or modify any of the steps shown in FIG. 11. One or more of the steps shown in FIG. 11 may be performed by any component or combination of components of sound processor 104.

In step 1102, an analysis channel associated with a frequency band is mapped to a stimulation channel that comprises four or more electrodes communicatively coupled to an auditory prosthesis associated with a patient. The analysis channel may be mapped to the stimulation channel in any suitable manner as may serve a particular implementation.

In step 1104, a spectral peak included in an audio signal presented to the patient is identified. The spectral peak may be identified in any of the ways described herein and may have a peak frequency included in a frequency band associated with the analysis channel mapped in step 1102.

In step 1106, the auditory prosthesis is directed to apply electrical stimulation representative of the spectral peak identified in step 1104 to a stimulation site associated with the peak frequency by simultaneously stimulating at least two of the four or more electrodes included in the analysis channel's corresponding stimulation channel at substantially fifty percent or less of their respective M levels in accordance with a multi-monopolar current steering strategy. Step 1106 may be performed in any suitable manner as may serve a particular implementation.

As described above, an exemplary system may include a sound processor (e.g., sound processor 104) and an auditory prosthesis implanted in a patient and selectively and communicatively coupled to the sound processor. The sound processor may be configured to map an analysis channel associated with a frequency band to a stimulation channel that comprises three electrodes communicatively coupled to the auditory prosthesis, identify a spectral peak included in an audio signal presented to the patient, the spectral peak having a peak frequency included in the frequency band, and direct the auditory prosthesis to apply electrical stimulation representative of the spectral peak to a stimulation site associated with the peak frequency by simultaneously stimulating at least two of the three electrodes at substantially fifty percent or less of their respective M levels in accordance with a tri-monopolar current steering strategy. Accordingly, the auditory prosthesis may operate at a compliance voltage substantially equal to fifty percent or less of a compliance voltage required for a maximum M level associated with the three electrodes (i.e., the highest M level out of the M levels associated with each respective electrode).

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
    mapping, by a sound processor, an analysis channel associated with a frequency band to a stimulation channel that comprises three electrodes communicatively coupled to an auditory prosthesis associated with a patient;
    determining, by the sound processor, a most comfortable current level ("M level") for each of the three electrodes;
    identifying, by the sound processor, a spectral peak included in an audio signal presented to the patient, the spectral peak having a peak frequency included in the frequency band; and
    directing, by the sound processor, the auditory prosthesis to apply electrical stimulation representative of the spectral peak to a stimulation site associated with the peak frequency by simultaneously stimulating at least two of the three electrodes at substantially fifty percent or less of their respective determined M levels in accordance with a tri-monopolar current steering strategy.

2. The method of claim 1, wherein the three electrodes comprise a first electrode having an associated first M level, a second electrode having an associated second M level, and a third electrode having an associated third M level, and wherein:
    a low cutoff frequency of the analysis channel corresponds to a position located in between the first and second electrodes;
    a center frequency of the analysis channel corresponds to a position of the second electrode; and
    a high cutoff frequency of the analysis channel corresponds to a position located in between the second and third electrodes.

3. The method of claim 2, wherein the peak frequency is substantially equal to the low cutoff frequency, and wherein the directing of the auditory prosthesis to apply electrical stimulation comprises directing the auditory prosthesis to simultaneously stimulate the first electrode at substantially fifty percent of the first M level and the second electrode at substantially fifty percent of the second M level.

4. The method of claim 2, wherein the peak frequency is substantially equal to the center frequency, and wherein the directing of the auditory prosthesis to apply electrical stimulation comprises directing the auditory prosthesis to simultaneously stimulate the first electrode at substantially twenty-five percent of the first M level, the second electrode at substantially fifty percent of the second M level, and the third electrode at substantially twenty-five percent of the third M level.

5. The method of claim 2, wherein the peak frequency is substantially equal to the high cutoff frequency, and wherein the directing of the auditory prosthesis to apply electrical stimulation comprises directing the auditory prosthesis to simultaneously stimulate the second electrode at substantially fifty percent of the second M level and the third electrode at substantially fifty percent of the third M level.

6. The method of claim 2, further comprising:
    mapping, by the sound processor, an additional analysis channel associated with an additional frequency band to an additional stimulation channel that comprises the second electrode, the third electrode, and a fourth electrode implanted in the patient and communicatively coupled to the auditory prosthesis;
    identifying, by the sound processor, an additional spectral peak included in the audio signal presented to the patient, the additional spectral peak having an additional peak frequency included in the additional frequency band; and
    directing, by the sound processor, the auditory prosthesis to apply electrical stimulation representative of the additional spectral peak to an additional stimulation site associated with the additional peak frequency by simultaneously stimulating at least two of the second, third, and fourth electrodes at substantially fifty percent or less of their respective M levels in accordance with the tri-monopolar current steering strategy.

7. The method of claim 2, wherein the first M level, the second M level, and the third M level are substantially equivalent.

8. The method of claim 2, wherein the first, second, and third electrodes are located adjacent one to another along an electrode lead implanted in the patient.

9. The method of claim 2, wherein a disabled electrode is disposed in between the first and second electrodes or the second and third electrodes.

10. The method of claim 2, wherein the first electrode comprises a most apical electrode, and wherein the method further comprises:
    identifying, by the sound processor, an additional spectral peak included in the audio signal, the additional spectral peak corresponding to a peak frequency that is lower than the low cutoff frequency;
    directing, by the sound processor, the auditory prosthesis to utilize phantom stimulation to apply electrical stimulation representative of the additional spectral peak.

11. The method of claim 2, wherein the third electrode comprises a most basal electrode, and wherein the method further comprises:
    identifying, by the sound processor, an additional spectral peak included in the audio signal, the additional spectral peak corresponding to a peak frequency that is higher than the high cutoff frequency;
    directing, by the sound processor, the auditory prosthesis to utilize phantom stimulation to apply electrical stimulation representative of the additional spectral peak.

12. The method of claim 1, further comprising directing, by the sound processor, the auditory prosthesis to operate at a compliance voltage substantially equal to fifty percent of a compliance voltage required for a maximum M level associated with the three electrodes.

13. A method comprising:
    mapping, by a sound processor, an analysis channel associated with a frequency band to a stimulation channel that comprises four or more electrodes communicatively coupled to an auditory prosthesis associated with a patient;
    determining, by the sound processor, a most comfortable current level ("M level") for each of the four or more electrodes;

identifying, by the sound processor, a spectral peak included in an audio signal presented to the patient, the spectral peak having a peak frequency included in the frequency band; and directing, by the sound processor, the auditory prosthesis to apply electrical stimulation representative of the spectral peak to a stimulation site associated with the peak frequency by simultaneously stimulating at least two of the four or more electrodes at substantially fifty percent or less of their respective determined M levels in accordance with a multi-monopolar current steering strategy.

14. A system comprising:
a mapping facility that maps an analysis channel associated with a frequency band to a stimulation channel that comprises at least three electrodes communicatively coupled to an auditory prosthesis associated with a patient;
a spectral analysis facility communicatively coupled to the mapping facility and that
  determines a most comfortable current level ("M level") for each of the at least three electrodes, and
  identifies a spectral peak included in an audio signal presented to the patient, the spectral peak having a peak frequency included in the frequency band; and
a stimulation strategy facility communicatively coupled to the spectral analysis facility and that directs the auditory prosthesis to apply electrical stimulation representative of the spectral peak to a stimulation site associated with the peak frequency by simultaneously stimulating at least two of the at least three electrodes at substantially fifty percent or less of their respective determined M levels in accordance with a multi-monopolar current steering strategy.

15. The system of claim 14, wherein the at least three electrodes comprise a first electrode having an associated first M level, a second electrode having an associated second M level, and a third electrode having an associated third M level, and wherein:
  a low cutoff frequency of the analysis channel corresponds to a position located in between the first and second electrodes;
  a center frequency of the analysis channel corresponds to a position of the second electrode; and
  a high cutoff frequency of the analysis channel corresponds to a position located in between the second and third electrodes.

16. The system of claim 15, wherein the peak frequency is substantially equal to the low cutoff frequency, and wherein the stimulation strategy facility is configured to direct the auditory prosthesis to apply electrical stimulation by directing the auditory prosthesis to simultaneously stimulate the first electrode at substantially fifty percent of the first M level and the second electrode at substantially fifty percent of the second M level.

17. The system of claim 15, wherein the peak frequency is substantially equal to the center frequency, and wherein the stimulation strategy facility is configured to direct the auditory prosthesis to apply electrical stimulation by directing the auditory prosthesis to simultaneously stimulate the first electrode at substantially twenty-five percent of the first M level, the second electrode at substantially fifty percent of the second M level, and the third electrode at substantially twenty-five percent of the third M level.

18. The system of claim 15, wherein the peak frequency is substantially equal to the high cutoff frequency, and wherein the stimulation strategy facility is configured to direct the auditory prosthesis to apply electrical stimulation by the auditory prosthesis to simultaneously stimulate the second electrode at substantially fifty percent of the second M level and the third electrode at substantially fifty percent of the third M level.

19. The system of claim 15, wherein the stimulation strategy facility is further configured to direct the auditory prosthesis to operate at a compliance voltage substantially equal to fifty percent or less of a compliance voltage required for a maximum M level associated with the at least three electrodes.

20. A system comprising:
a sound processor; and
an auditory prosthesis implanted in a patient and selectively and communicatively coupled to the sound processor;
wherein the sound processor
  maps an analysis channel associated with a frequency band to a stimulation channel that comprises at least three electrodes communicatively coupled to the auditory prosthesis,
  determines a most comfortable current level ("M level") for each of the at least three electrodes,
  identifies a spectral peak included in an audio signal presented to the patient, the spectral peak having a peak frequency included in the frequency band, and
  directs the auditory prosthesis to apply electrical stimulation representative of the spectral peak to a stimulation site associated with the peak frequency by simultaneously stimulating at least two of the at least three electrodes at substantially fifty percent or less of their respective determined M levels in accordance with a multi-monopolar current steering strategy; and
wherein the auditory prosthesis operates at a compliance voltage substantially equal to fifty percent or less of a compliance voltage required for a maximum determined M level associated with the at least three electrodes.

* * * * *